United States Patent
Schiødt

(10) Patent No.: US 6,706,914 B2
(45) Date of Patent: Mar. 16, 2004

(54) RHODIUM CONTAINING SOLUTIONS

(75) Inventor: Niels Christian Schiødt, Brønshøj (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 10/277,915

(22) Filed: Oct. 23, 2002

(65) Prior Publication Data

US 2003/0050505 A1 Mar. 13, 2003

Related U.S. Application Data

(63) Continuation of application No. 09/853,911, filed on May 11, 2001, now abandoned.

(30) Foreign Application Priority Data

May 18, 2000 (DK) .................................... 2000 00802

(51) Int. Cl.$^7$ ............................................... C07C 51/00
(52) U.S. Cl. ............................................ 562/1; 560/129
(58) Field of Search ................................ 560/129, 522, 560/512, 607; 502/224, 229

(56) References Cited

U.S. PATENT DOCUMENTS

| 3,965,192 A | | 6/1976 | Booth |
| 4,195,042 A | * | 3/1980 | Zuech ........................ 568/454 |
| 4,340,570 A | * | 7/1982 | Davidson .................... 502/26 |
| 4,341,741 A | | 7/1982 | Davidson et al. |
| 4,376,724 A | | 3/1983 | Mita et al. |
| 4,420,420 A | | 12/1983 | Mita et al. |
| 4,550,096 A | | 10/1985 | Page et al. |
| 5,051,522 A | | 9/1991 | Konkol et al. |

FOREIGN PATENT DOCUMENTS

| DE | 3115032 | 7/1991 |
| DK | 164815 | 8/1992 |
| JP | 56 144 747 | 11/1981 |
| JP | 63041892 | 7/1982 |
| JP | 5 818147 | 4/1983 |
| JP | 62 148437 | 7/1987 |
| JP | 63 227 531 | 8/1988 |
| JP | 1025525 | 1/1998 |
| NR | 169342 | 3/1992 |

OTHER PUBLICATIONS

CA:126:74405 abs of Journal of Molecular Catalysis A: Chemic by Kilner et al 112(3) pp 327–345, 1996.*

* cited by examiner

Primary Examiner—Jean F. Vollano
(74) Attorney, Agent, or Firm—Dickstein Shapiro Morin & Oshinsky, LLP

(57) ABSTRACT

A method for generating a concentrated solution of rhodium starting from solid $RHI_3$ and other solid rhodium sources by combination with a reducing agent, preferably hydrazine and hydrazine derivatives. The solution does not form any precipitate of rhodium iodide or other compounds even upon admixture with large quantities of hydriodic acid. The solution is stable at ambient conditions, very stable towards air and is easily prepared without application of external pressure and heating sources.

8 Claims, No Drawings

RHODIUM CONTAINING SOLUTIONS

This is a continuation of U.S. Pat. application Ser. No. 09/853,911, filed May 11, 2001, now abandoned.

FIELD OF THE INVENTION

The field to which this invention pertains is generation and regeneration of a rhodium containing solution. This solution can be used as a catalyst precursor for the industrial manufacture of acetic acid, acetic anhydride, ethylidene diacetate and related processes utilising compounds of rhodium.

BACKGROUND OF THE INVENTION

For the industrial production of acetic acid, carbonylation of methanol has long been the preferred method. Dimethyl ether and methyl acetate and mixtures of these two components may also be used as feed, optionally admixed with methanol. These reactions are catalysed by certain transition metals together with iodide in the form of methyl iodide and/or hydriodic acid. Of the transition metals, rhodium and iridium are preferred due to their high activity and selectivity. In industrial plants, the metal catalyst exists in a dissolved form during operation of the plant. In those cases, where the catalyst is rhodium, it is generally recognised that the predominant rhodium containing specimen present under the conditions of operation is the anionic complex $[Rh(CO)_2I_2]^-$. This complex is formed—in the form of the acid or as a salt—from virtually any rhodium source under the conditions of operation (at a temperature above 150° C. and at least 5 bar ($5·10^5$ Pa) CO-pressure).

The currently preferred rhodium source for start-up of acetic acid and acetic anhydride plants is rhodium iodide, $RhI_3$, which in pure form appears as a black solid. It is not desirable to transfer it to the reactor zone in an undissolved form, since the dissolution of this compound under the conditions of operation takes some time, and several complications may occur before the dissolution is complete. Rhodium iodide, however, is well known to be practically insoluble at ambient conditions. Thus water, acetic acid, methanol, methylacetate and other common solvents have no effect on $RhI_3$. Although it has some solubility in hydriodic acid, the solubility is low, and very high concentrations of hydriodic acid are necessary. Other rhodium compounds are more soluble, e.g. $RhCl_3$, but they precipitate upon admixture with solutions of hydriodic acid due to reaction with the iodide ions present in the solution. Thus, since iodide is needed as a co-catalyst, $RhI_3$ precipitates in the reactor upon admixture of a $RhCl_3$ solution with the iodine containing co-catalyst solution. Certain complexes of rhodium are known to be more stable in the presence of iodide, but they are not preferred since they are generally costly and difficult to handle. Some of these compounds furthermore contain elements or molecular entities, the presence of which may be undesirable. Examples are sulphur, chlorine, bromine and arsenic containing complexes. Even though rhodium iodide may react with reducing agents and thus be brought into solution, such solutions are often sensitive towards air, which may re-oxidise rhodium and thus reprecipitate $RhI_3$. Another problem pertains to rhodium being fairly noble, thus the admixture of rhodium iodide with strong reducing agents may potentially cause over-reduction to elemental rhodium.

It is well known that dissolution of $RhI_3$ is accomplished under certain circumstances by reduction in the presence of a solvent. Such reduction may be carried out with hydrogen or carbon monoxide or synthesis gas at elevated temperatures and pressure, in which case the active form of the catalyst $[Rh(CO)_2I_2]^-$ is formed directly according to the equation $$RhI_3 + 3\ CO + H_2O = H[Rh(CO)_2I_2] + CO_2 + HI$$

The solution thus obtained is stable towards high concentrations of iodide, but only as long as a minimum pressure of carbon monoxide is maintained and only as long as air and other oxidising agents are avoided. This is the method of current practice in the art of catalyst generation for rhodium catalysed acetic acid production.

Obviously, this method is tedious and costly since the catalyst solution must be prepared under pressure and with applied heat and also must be transferred to the methanol carbonylation reactor under pressure. Furthermore, it is well known that rhodium iodide (probably in an impure form) precipitates in certain parts of the internals of acetic acid plants during operation. Due to the very high price of rhodium, it is feasible to regenerate the catalyst from these solid precipitates. Regeneration of the catalyst solution from the solid may be carried out in the same way as described above for start-up.

A more preferable catalyst formulation would be a solution containing rhodium and iodide in high concentrations. This solution should be stable towards precipitation of $RhI_3$, stable on exposure to air and water, and should not contain undesired elements such as sulphur, arsenic and the like. Such a catalyst formulation would allow for easy and less expensive transportation and simple transfer to the reactor.

As explained above, however, such a catalyst formulation is very hard to achieve. It was therefore highly surprising to discover that solid $RhI_3$ dissolves with hydrazine hydrate and particularly that solutions with a very high concentration of rhodium can be formed and are stable for at least several months.

The present invention thus provides a method for generating a concentrated solution of rhodium starting from solid $RhI_3$ and other solid rhodium sources by combination with a reducing agent, preferably hydrazine and hydrazine derivatives. Said solution does not form any precipitate of rhodium iodide or other compounds even upon admixture with large quantities of hydriodic acid. Said solution is stable at ambient conditions, very stable towards air and is easily prepared without application of external pressure and heating sources.

The use of hydrazine and other reducing agents for the activation of rhodium containing catalysts has been claimed in a number of patents: JP 63/227531 A, JP 87/60062 A, JP 62/148437 A, JP 85/289269 A, JP 88/041892 B, JP 56/144747 A, DE 3,115,032 A, U.S. Pat. No. 4,376,724 A, JP 83/018147 B, U.S. Pat. No. 4,420,420 A, DE 3,115,032 C. The known technique, however, claims use of a reducing agent for activating a solid (heterogeneous) rhodium containing catalyst without the catalyst being dissolved. Obviously, it is not the intention of the processes described in the above patents to prepare rhodium containing solutions.

Some other patents claim the use of rhodium and hydrazine in combination to form homogeneous catalysts. Thus, NO 169342 B, DK 164815 B and U.S. Pat. No. 4,550,096 teach the preparation of homogeneous hydrogenation catalysts and U.S. Pat. No. 5,051,522 teaches the use of hydrazine to prepare a hydroformylation catalyst. None of these patents pertain to the field of methanol carbonylation, however, and the stabilities of the rhodium catalysts toward iodide are not discussed.

A process for recovering Group VIII noble metals by extraction with amines, including the use of hydrazine, is claimed in U.S. Pat. No. 4,341,741. According to this patent, noble metals such as rhodium and iridium used in the carbonylation of methyl acetate and dimethyl ether, accumulate in a residue formed during the carbonylation reaction, containing typically 0–4% wt/wt rhodium. A sample containing 1% Rh was at first partly extracted with dilute hydrochloric acid and methylene chloride, leading to a 0.5% Rh content in the residue. Ten (10) miligram of the acid extracted residue was then dissolved in 5 ml methyl acetate and treated with 0.1 ml of hydrazine hydrate. It was demonstrated that more than 85% of the residue-bound Rh was extracted this way. However, the concentration of rhodium in the extract was no more than 0.01 g/l or less than $0.1 \cdot 10^{-3}$ M. Typical rhodium concentrations in an acetic acid plant reactor are $1.0 \cdot 10^{-3}$ M, and a catalyst solution should preferably be even more concentrated to facilitate transport and start-up.

The rhodium containing solutions of the present invention carry up to as much as 0.34 M rhodium, and have furthermore been demonstrated to be stable for long periods of time. Even by addition of an iodide source, a high concentration of rhodium (at least 0.03 M) can be maintained.

SUMMARY OF THE INVENTION

The invention concerns a method for generating a solution containing rhodium at a concentration of at least 0.01 M, obtained by treating solid $RhI_3$ or other solid source of rhodium with a reducing agent selected from a source of hydrazine, hydrazine hydrate, hydrazinium salts, organic derivatives of hydrazine, hypophosphorous acid and salts of hypophosphorous acid. Optionally, a co-solvent can be added, at normal pressure and without the use of carbon monoxide and synthesis gas.

The invention also concerns the use of the method stated above, for the regeneration of rhodium catalyst from industrial plants producing acetic acid and derivatives thereof.

The invention concerns moreover a solution containing rhodium at a concentration of at least 0.01 M, which is preparable by the method mentioned above.

Another aspect of the invention concerns the use of the solution mentioned above as a catalyst source.

Finally, it is also the intention to provide a product which is made available by isolation of a rhodium containing solid from a solution obtained by the method according to the invention.

DESCRIPTION OF THE INVENTION

It is the intention of the present invention to provide a method for the generation and regeneration of a solution containing rhodium at a concentration of at least 0.01 M. The method of the present invention comprises steps of treating solid rhodium (III) iodide or another rhodium containing solid with a reducing agent under ambient conditions, thereby causing complete dissolution of the rhodium source. This operation may beneficially be carried out with the rhodium containing solid suspended in water, acetic acid or another solvent before addition of the reducing agent and optionally the complexing agent.

As reducing agents, hydrazine and hypophosphorous acid have the desired effect of dissolving rhodium iodide. Hydrazine is presently particularly preferred since complete and instant dissolution of $RhI_3$ is accomplished without the need for an external source of heat (the reaction between rhodium iodide and hydrazine is exothermic). Hydrazine in the reactor will not alter activity or selectivity. During the conditions of operation it will most likely react to ammonium iodide and primary, secondary, tertiary and quaternary methyl ammonium iodide salts. These salts have a high solubility in the reaction medium and will not alter the process in the low amounts needed to generate and regenerate rhodium solutions. In the following examples, hydrazine hydrate has been used as the source of hydrazine.

Thus, the preferred method of this invention for generating a rhodium containing solution consists of treating the solid rhodium source (e. g., $RhI_3$) with hydrazine hydrate; optionally admixed with a co-solvent. Other solid sources of rhodium include rhodium chloride, rhodium bromide, rhodium nitrate, rhodium acetate, rhodium oxide, and rhodium sulphate.

This method is inexpensive and easy to carry out. The method provides a rhodium containing solution, which is infinitely stable towards air under ambient conditions, which does not precipitate rhodium iodide upon addition of hydriodic acid or other iodide sources and which may contain rhodium in concentrations of at least 0.01 M. Furthermore, the solution does not contain elements, which are not usually present in acetic acid plants apart from small amounts of nitrogen, which does not cause any damage or problems during operation of such plants.

Thus, one part of $RhI_3$ (by weight) is instantly dissolved upon admixture with 2 parts (by weight) of hydrazine hydrate to give an orange solution. The dissolution happens without application of heat apart from that evolved in the course of the reaction. Provided a small excess of hydrazine is present, this solution does not form a precipitate even upon admixture with a large amount of hydriodic acid.

A practical application of the invention would be to use a solution containing a reducing agent selected from hydrazine, hydrazine derivatives, hydrazinium salts, hypophosphorous acid and hypophosphite salts, to dissolve rhodium containing precipitates in the internals of an acetic acid plant, without removing the precipitate from the location inside the plant.

The rhodium solution obtained by the method according to the invention can also be used in a process for the production of both carboxylic acids such as, for example, acetic acid, and for their derivatives, whereby the corresponding alcohol is carbonylated. This would involve a step, whereby the carboxylic acid is contacted with the corresponding alcohol in the presence of the rhodium solution, which thereby acts as a catalyst source for the reaction.

EXAMPLES

Preparation of Rhodium Containing Solutions.

Example 1

$RhI_3$ (0.05 g) is treated with liquid hydrazine hydrate $NH_2NH_2 \cdot H_2O$ (0.10 g). The black powder obtained thereby dissolves completely to yield a clear, orange solution.

Example 2

The solution prepared in Example 1 is treated with hydriodic acid (0.5 g 57% w/w aqueous solution). A small amount of dark brown precipitate forms, which partly dissolves on the application of heat. By addition of 0.3 g hydrazine hydrate, dissolution is complete and the mixture appears as a clear, orange solution. The volume of the solution is 0.9 ml giving [Rh]=0.11 M.

Example 3

The solution prepared in Example 2 is treated with additionally 2.5 g of 57% hydriodic acid. The colour turns dark red, but no precipitate forms. Extraction with n-heptane demonstrates that no free iodine is present in the solution. [Rh]=0.03 M.

Example 4

$RhI_3$ (0.05 g) is treated with hydrazine hydrate (0.40 g). A clear, orange solution arises. Hydriodic acid (3.0 g, 57%) is added. The mixture turns dark red, but remains homogeneous without formation of a precipitate. [Rh]=0.03 M.

Example 5

$RhI_3$ (0.05 g) is dissolved by the addition of hydrazine hydrate (0.40 g). A solution of 0.50 g anhydrous lithium iodide in concentrated hydriodic acid (2.50 g 57%) is added, causing the colour to change to dark red. The dark colour and the formation of foam prohibits the observation of whether or not a precipitate has formed. Upon dilution with 1.0 g glacial acetic acid the foaming decreases, revealing a small amount of dark precipitate. This precipitate dissolves on addition of 0.30 g hydrazine hydrate.

Example 6

$RhI_3$ (0.55 g) is suspended in 2.0 g of glacial acetic acid. 2.00 g of hydrazine hydrate are added dropwise to the suspension causing a vigorous reaction with evolution of gas. Very shortly after the addition of hydrazine hydrate, a clear, homogeneous orange solution with a volume of approx. 4 ml is observed with no trace of undissolved particles. An amount of 1.00 g of this solution is withdrawn and stored at room temperature in contact with air for 8 months without any apparent changes.

Example 7

$RhI_3$ (0.50 g) is treated with 1.00 g hydrazine hydrate resulting in a clear, orange solution. Upon the addition of 2.00 g glacial acetic acid, a red precipitate forms. This precipitate dissolves on heating to give a dark red solution. No precipitate forms upon cooling to room temperature. The volume of this solution is 3 ml, corresponding to a rhodium concentration of [Rh]=0.34 M.

Example 8

$RhI_3$ (0.05 g) is treated with 0.50 g hypophosphorous acid ($H_3PO_2$, 50% w/w aqueous solution). By the application of low heat, a dark brown solution arises.

Example 9

The solution prepared in Example 7 is treated with hydriodic acid (0.50 g 57% aqueous solution). A dark precipitate is formed. Additional hypophosphorous acid solution (0.50 g 50% aqueous solution) is added and by gentle heating, the amount of precipitate seemingly diminishes. Dilution with glacial acetic acid (1.0 g) results in a dark, olive brown solution.

Activity and Selectivity of a Rhodium Containing Solution.

Example 10

The solution prepared in Example 6 was diluted with glacial acetic acid until a total mass of 5.00 g was obtained. Of this solution, 0.50 g (corresponding to 0.055 g $RhI_3$) was transferred to a Hastelloy C autoclave equipped with stirrer, thermosensor and external heating device, and connected to a CO-reservoir. The pressure in the CO-reservoir was measured continuously, allowing observation of the rate of CO-consumption.

The catalyst solution in the autoclave was admixed with 29.03 g acetic acid, 11.98 g methyl acetate, 13.13 g demineralized water and 7.17 g methyl iodide. The autoclave was sealed, pressurised with carbon monoxide to 10 bar ($10^6$ Pa), heated to 185° C., connected to the CO-reservoir and pressurised to 36 bar ($36 \cdot 10^5$ Pa) total pressure. The consumption of carbon monoxide was linear in time. In 30 minutes, the pressure decrease in the CO-reservoir was 206 psi (1420 kPa), corresponding to a TurnOver Frequency (mole CO consumed per mole Rh per unit time) of $0.50\ s^{-1}$ The autoclave was cooled and the content was analysed by gas chromatography, showing that the selectivity to acetic acid/methyl acetate was above 99.5%.

Example 11

This example was carried out as described in Example 10, but with the following amounts: 0.50 g rhodium solution, 29.07 g acetic acid, 12.13 g methyl acetate, 13.11 g demineralized water and 7.14 g methyl iodide. At 185° C. and 35 bar (35–105 Pa) total pressure, the pressure decrease in the CO-reservoir over 30 minutes was 219 psi (1510 kPa) corresponding to a TurnOver Frequency of 0.53 so. The autoclave was cooled and the content was analysed by gas chromatography showing that the selectivity to acetic acid/methyl acetate was above 99.5%.

Comparative Example 12

This example was carried out as described in Example 10, with the exception that the rhodium source in this case was solid rhodium iodide (0.037 g $RhI_3$). This was admixed with 28.80 g acetic acid, 12.19 g methyl acetate, 12.97 g demineralized water and 7.22 g methyl iodide. At 185° C. and 35 bar (35–105 Pa) total pressure, the pressure decrease in the CO-reservoir over 30 minutes was 142 psi (979 kPa) corresponding to a TurnOver Frequency of $0.51\ s^{-1}$ The autoclave was cooled and the content was analysed by gas chromatography showing that the selectivity to acetic acid/methyl acetate was above 99.5%.

What is claimed is:

1. A method for generating carboxylic acids using a carbonylation catalyst source solution containing rhodium at a concentration of at least 0.01 M, the method comprising the steps of:

treating solid rhodium iodide ($RhI_3$) with a reducing agent selected from a source of hydrazine, hydrazine hydrate, hydrazinium salts, organic derivatives of hydrazine, hypophosphorous acid and salts of hypophosphorous acid to produce a catalyst source solution; and catalyzing production of a carboxylic acid using the catalyst source solution.

2. A method as claimed in claim 1, where the solution obtained has a concentration of rhodium of at least 0.20 M.

3. A method as claimed in claim 1, further comprising the step of addition of a co-solvent selected from water and organic solvents to the catalyst source solution.

4. The method of claim 1, wherein the solution is used as a catalyst source for the production of acetic acid.

5. A method for generating acetic anhydride or ethylene diacetate using a carbonylation catalyst source solution containing rhodium at a concentration of at least 0.01 M, the method comprising the steps of:

treating solid rhodium iodide $RhI_3$ with a reducing agent selected from a source of hydrazine, hydrazine hydrate, hydrazinium salts, organic derivatives of hydrazine, hypophosphorous acid and salts of hypophosphorous acid to produce a catalyst source solution; and catalyzing production of acetic anhydride or ethylene diacetate using the catalyst source solution.

6. The method of claim 5, wherein the solution is used as a catalyst source for the production of acetic anhydride.

7. The method of claim 5, wherein the solution is used as a catalyst source for the production of ethylene diacetate.

8. The method of claim 1, wherein a source of rhodium is an industrial plant producing acetic acid, the method including the step of regenerating rhodium catalyst as the rhodium source.

* * * * *